(12) United States Patent
Takahashi (10) Patent No.: US 6,974,240 B2
(45) Date of Patent: Dec. 13, 2005

(54) ILLUMINATION CONTROL SYSTEM AND ILLUMINATION CONTROL METHOD FOR ENDOSCOPE SYSTEMS

(75) Inventor: Tomoya Takahashi, Akiruno (JP)

(73) Assignee: Olympus Corporation, Tokyo (JP)

( * ) Notice: Subject to any disclaimer, the term of this patent is extended or adjusted under 35 U.S.C. 154(b) by 46 days.

(21) Appl. No.: 10/726,938

(22) Filed: Dec. 3, 2003

(65) Prior Publication Data

US 2004/0109319 A1 Jun. 10, 2004

Related U.S. Application Data

(63) Continuation of application No. PCT/JP02/11090, filed on Oct. 25, 2002.

(30) Foreign Application Priority Data

Oct. 26, 2001 (JP) ........................................ 2001-329565

(51) Int. Cl.[7] .............................................. A61B 1/045
(52) U.S. Cl. ..................... 362/574; 362/293; 600/178; 600/180; 600/181
(58) Field of Search ................................ 362/292, 282, 362/283, 284, 323, 324, 572, 574; 600/178, 180, 181

(56) References Cited

U.S. PATENT DOCUMENTS 5,917,558 A * 6/1999 Stanton ....................... 348/743
6,126,593 A * 10/2000 Honda et al. ................ 600/180
6,477,403 B1 * 11/2002 Eguchi et al. ............... 600/478
6,622,053 B1 * 9/2003 Hewlett et al. ............... 700/19
2004/0267091 A1 * 12/2004 Imaizumi et al.

FOREIGN PATENT DOCUMENTS

| JP | 1-170436 | 7/1989 |
| JP | 6-245900 | 9/1994 |
| JP | 9-197294 | 7/1997 |
| JP | 2882609 | 2/1999 |

OTHER PUBLICATIONS

English translation of Japanese Patent Laid–open No. Hei 1–170436 Gazette, published Jul. 5, 1989.

* cited by examiner

*Primary Examiner*—Laura K. Tso
(74) *Attorney, Agent, or Firm*—Scully, Scott & Murphy & Presser

(57) ABSTRACT

An illumination control system comprises a rotation detecting section, an abnormality determination section, and a filter removing section. The rotation detecting section detects the rotational driving of a filter which is located on a path of illumination light emitted from a light source, which irradiates color light rays having different wavelengths to an object, and which is driven by a rotational driver. The abnormality determination section determines whether status of filter rotation is normal or abnormal based on the detected rotation of the filter by the rotation detecting section. The filter removing section removes the filter from the path of the illumination light when the abnormality determination section determines that the status of filter rotation is abnormal.

16 Claims, 7 Drawing Sheets

FIG.4A  WSP

FIG.4B  CPUFLASH

ILLUMINATION CONTROL SYSTEM AND ILLUMINATION CONTROL METHOD FOR ENDOSCOPE SYSTEMS

CROSS REFEERENCE TO RELATED APPLICATION

This application is a continuation of PCT application no. PCT/JP02/11090 filed on Oct. 25, 2002, the entire contents of which is incorporated herein by its reference.

TECHNICAL FIELD

The present invention relates to an illumination control system and an illumination control method for endoscope systems according to when the rotation of a rotary color filter included in a light source device that supplies illumination light to an endoscope becomes abnormal.

BACKGROUND ART

In the past, electronic endoscope systems including a solid-state imaging device, for example, a charge-coupled device or a CMOS imaging device (generically referred to as a CCD) have been widely employed in the fields of medicine and industries alike. Among the electronic endoscope systems, the electronic endoscope system employed in the field of medicine is requested to have an insertion member thereof, which is inserted into a body cavity, made thinner. Moreover, the electronic endoscope system is requested to have the CCD made small-sized and designed to provide a larger number of pixels because of the necessity of producing a video signal that offers a high resolution.

Electronic endoscopes adopting the CCD fall into two types in terms of a method of producing a color video signal. One type of electronic endoscope uses a color filter to split light reflected from an object into three color light rays of red (R), green (G), and blue (B). CCDs produce image signals from the resultant red, green, and blue light rays at the same time. The other type of electronic endoscope adopts a so-called field-sequential technique that emits color illumination light rays of red, green, and blue to an object, and uses a single CCD to produce video signals from the color illumination light rays.

In order to make an insertion member included in an endoscope system thinner, the field-sequential technique is preferred. Besides, a video signal capable of providing a high resolution can be produced.

An electronic endoscope system adopting the field-sequential technique has been disclosed in Japanese Patent No. 2882609. The endoscope system disclosed in the Japanese Patent No. 2882609 will be described in conjunction with FIG. 5. An electronic endoscope system 51 comprises an endoscope 52, a light source device 53, a control device 54, and a TV monitor 55.

Figure 5:
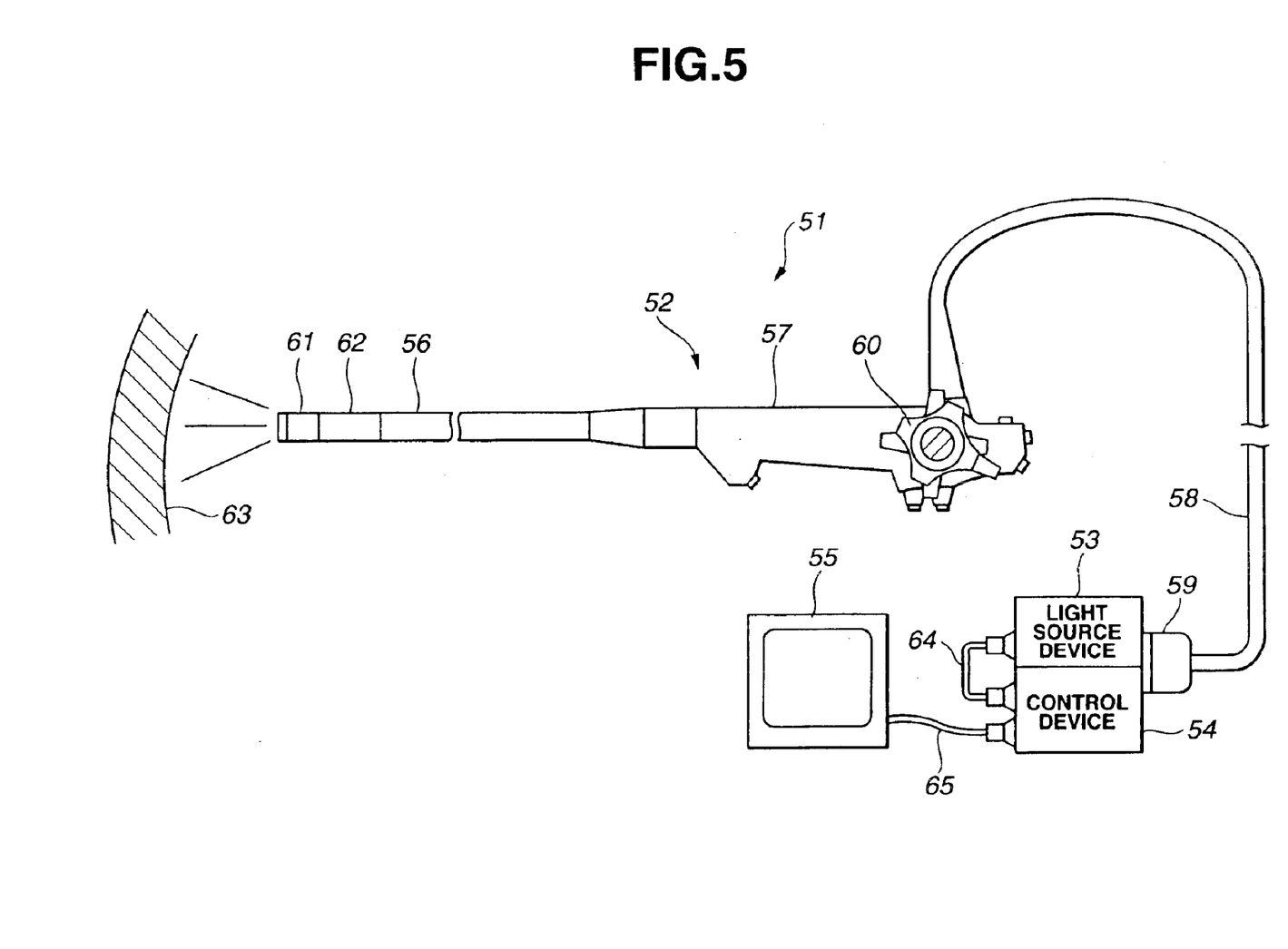
FIG. 5 is an explanatory diagram concerning a conventional endoscope system.

The endoscope 52 has an elongated insertion member 56 that is formed with a flexible member and inserted into a body cavity, and an operating member 57 proximal to the insertion member 56. A distal section 61 and a bending section 62 are successively joined to form the distal portion of the insertion member 56. The operating member 57 includes an operation knob 60 used to bend the bending section 62 of the insertion member 56. Moreover, the operating member 57 has a forceps port that communicates with a forceps insertion guide channel lying through the insertion member 56, and a knob used to supply water or air to a water/air supply nozzle, which is located in the distal section 61, over a water/air supply channel. Besides, one end of a universal cord 58 that connects the light source device 53 and the control device 54 is coupled to the operating member 57.

The light source device 53 includes a light source that emanates white light, such as, a xenon lamp, a lighting/driving mechanism that controls the lighting or driving of the light source, and a color filter that converts white light emitted from the light source into color light rays of red, green, and blue. Illumination light emanating from the light source device 53 is propagated over a light guide lying through the universal cord 58 and endoscope 52 alike, and irradiated to an object 63 from the distal section 61 of the insertion member 56.

The control device 54 has the ability to control the driving of a CCD incorporated in the distal section 61 of the insertion member 56. The control device 54 also has the ability to capture video signals, which the CCD produces from the red, green, and blue illumination light rays emitted from the light source device 53, and the ability to produce a predetermined television video signal from the red, green, and blue video signals.

On the TV monitor 55, a reproduced image based on the television video signal produced by the control device 54 is displayed.

The configuration of the light source device 53 will be described in conjunction with FIG. 6. White light emitted from the light source. 74 such as a xenon lamp is passed through a RGB rotary filter 73 that has color transmission filters 73R, 73G, and 73B for red, green, and blue arranged on the perimeter thereof. The white light falls on the proximal end surface of the light guide 19 via a condenser lens 75.

The RGB rotary filter 73 is driven to rotate at a predetermined rps by means of a motor 72. Light rays successively passed through the color transmission filters 73R, 73G, and 73B for red, green, and blue fall on the light guide 19.

The successive light rays of red, green, and blue falling on the light guide 19 are propagated over the universal cord 58, operating member 57, and insertion member 56, and then irradiated to the object 63 from the distal section 61.

A motor drive circuit 71 controls the rotational driving of the motor 72. The motor 72 has a frequency generator (FG) 72A. Pulses FG are produced with a rotation of the motor 72. This is attributable to electromotive force generated with a rotation of a magnet incorporated in the motor 72. For example, twenty-five pulses FG are produced with one rotation of the motor 72. The rotational frequency of the motor 72 will be discussed using the unit of fsc. The pulse frequency at which the frequency oscillator 72A produces pulses is 25 fsc. The pulse frequency of the frequency oscillator 72A is reported to a speed control circuit 77. Pulses produced at a pulse frequency of 4 fsc by a 4 fsc oscillator 78 are transferred at a one-sixth of the input frequency by a ⅙ frequency divider 44, that is, at a pulse frequency of ⅔ fsc. The pulse frequency of ⅔ fsc serves as a reference frequency that is compared with the pulse frequency of the frequency oscillator 72A. When the pulse frequency deviates from the reference frequency of ⅔ fsc, a rotating speed error voltage is produced.

On the other hand, the RGB rotary filter 73 has three silk-like reflectors 41r, 41g, and 41b arranged equidistantly concentrically. The reflectors give indices indicating open periods during which the color transmission filters 73R, 73G, and 73B for red, green, and blue are used. Sensors 42a and 42b are opposed to the reflectors 41r, 41g, and 41b. A pulse generated when the sensors 42a and 42b detects the reflector 41r, 41g, or 41b has the wave thereof reshaped by a pulse reshaping circuit 43. The resultant pulse is transferred to a phase comparing circuit 84.

The phase comparing circuit 84 receives pulses that have been produced at the pulse frequency of 4 fsc by the 4 fsc oscillator 78 and transferred at a quarter of the input frequency by a ¼ frequency divider 79. Furthermore, the phase comparing circuit 84 receives a vertical synchronizing (sync) signal (VD) from the control device 54.

To be more specific, a period during which the color transmission filters 73R, 73G, and 73B included in the rotary filter 73 transmit light corresponds to an exposure period during which the CCD is exposed. A period during which light is intercepted by the portion of the rotary filter 73 surrounding the color transmission filters 73R, 73G, and 73B corresponds to a period during which charge accumulated in the CCD is read into the control device 54 and a video signal is produced. In order to match the timing of the video signal with the timing of rotating the rotary filter 73, the phase of pulses produced when the sensors 42a and 42b detect the reflectors 41r, 41g, and 41b, the phase of the vertical sync signal VD contained in the video signal sent from the control device 54, and the phase of pulses transferred at the reference frequency fsc from the ¼ frequency divider 79 are compared with one another. Consequently, a phase error voltage is produced.

The speed error voltage produced by the speed control circuit 77 and the phase error voltage produced by the phase comparing circuit 84 are added up by an adder 85. Based on the resultant voltage, the motor drive circuit 71 controls the rotational driving of the motor 72.

Figure 7:
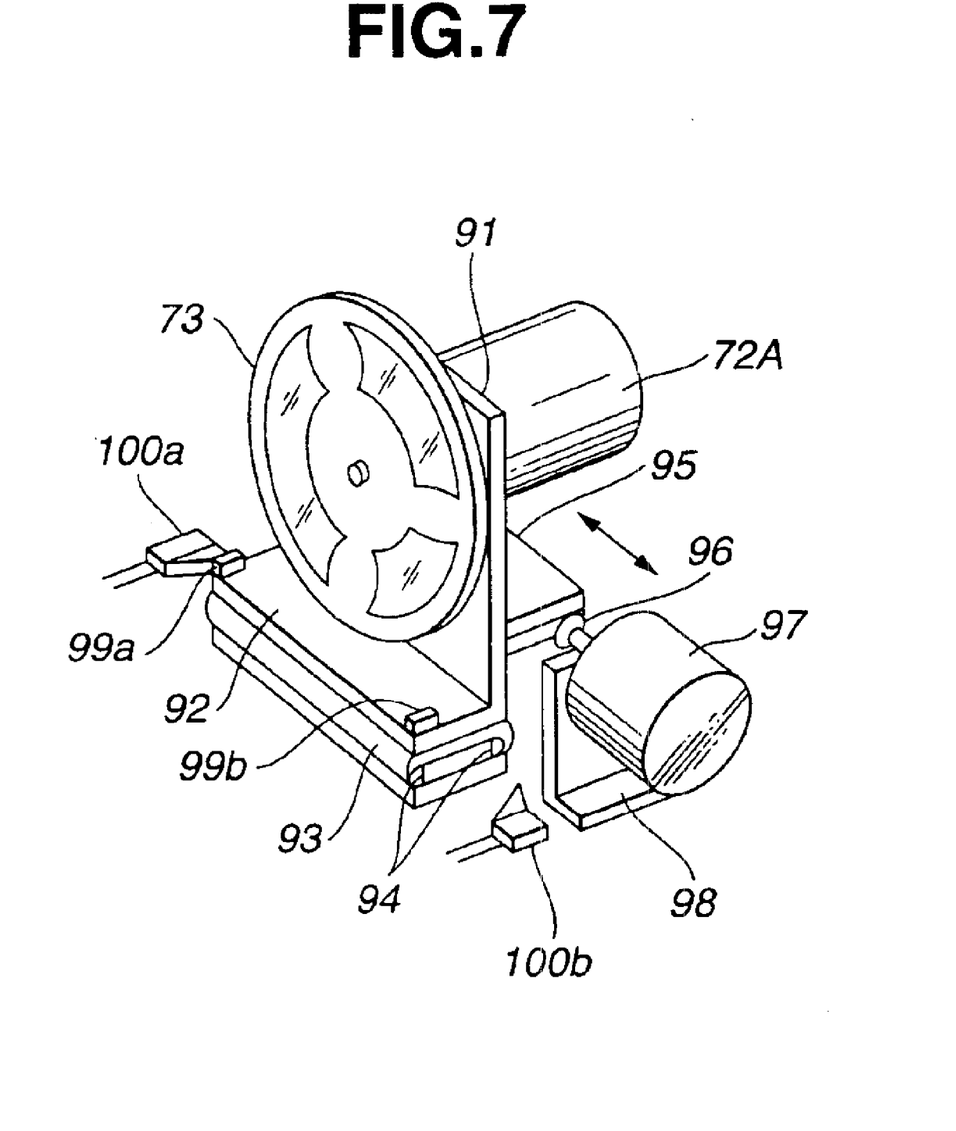
FIG. 7 is a perspective view showing the components of a rotary filter employed in the conventional endoscope system and presenting a removing mechanism.

Moreover, a type of endoscope other than the field-sequential type may be adopted as the endoscope 52. Japanese Unexamined Patent Application Publication No. 9-197294 has disclosed an endoscope in which the rotary filter 73 and motor 72 are removed from the path along which light emanating from the light source 74 is propagated to the light guide 19 via the condenser lens 75. In order to remove the rotary filter 73 and motor 72 from the light path, they are disposed as shown in FIG. 7. Namely, the rotary filter 73 and motor 72 are fixed to an L-shaped mounting bracket 91. Two rails 94, 94 are fixed to the bottom of a flange 92 that is a horizontally bent lower portion of the mounting bracket 91 while being parallel to each other. A sliding member 93 is attached to the bottom of the flange 92 so that it will enclose the rails 94 from the sides of the rails 94, 94. In other words, the sliding member 93 of the bracket 91 is attached so that it can freely slide in directions of arrows in FIG. 7 along the rails 94, 94.

A rack 95 is fixed to the side of the mounting bracket 91 on which the motor 72 is mounted. A worm gear 96 that is rotated by a motor 97 is meshed with the rack 95. By driving the motor 97 to rotate it forwards or reversely, the mounting bracket 91 slides in the directions of arrows in FIG. 7 by means of the worm gear 96 and rack 95.

Furthermore, switch pressers 99a and 99b are located at both ends of the flange 92 of the mounting bracket 91. Micro-switches 100a and 100b are opposed to the switch pressers 99a and 99b. The micro-switches 100a and 100b are located at a position at which the rotary filter 73 fixed to the mounting bracket 91 lies when moved to the path of light emanating from the light source 74 and a position at which the rotary filter 73 lies when removed from the path of light emanating from the light source 74.

Owing to the foregoing structure, depending on an object imaging technique implemented in the endoscope 52, the rotary filter 73 can be readily removed from the path of light emanating from the light source 74.

In the aforesaid conventional field-sequential type electronic endoscope system, the rotary filter 73 is disposed on the light path linking the light source 74 included in the light source device 53, the condenser lens 75, and the proximal end of the light guide 19 incorporated in the universal cord 58 coupled to the light source device 53. With the rotation of the motor 72, white light emitted from the light source 74 is passed through the red, green, and blue transmission filters 73R, 73G, and 73B included in the rotary filer 73. The resultant light is irradiated to the object 63 from the distal section 61 of the endoscope 52 over the light guide 19. The CCD incorporated in the distal section 61 of the insertion member 56 is exposed to reflected light rays of the red, green, and blue light rays which are reflected from the object illuminated with the red, green, and blue irradiation light rays. Consequently, red, green, and blue video signals are produced.

While the electronic endoscope system 51 is used to diagnose a body cavity, the rotational driving of the rotary filter 73 may be stopped for some reasons. When the rotary filter 73 is stopped rotating, for example, the red transmission filter 73R lies on the light path, an object picture signal produced by the CCD contains a red picture signal alone. When the rotary filter 73 is stopped rotating, for example, the non-transmission area of the rotary filter 73 between the red transmission filter 73R and green transmission filter 73G which does not transmit illumination light may lie on the light path. In this case, when the rotary filter is stopped during a period during which light is passed through the red transmission filter 73R and a red video signal is read, illumination light emanating from the light source 74 is intercepted by the non-transmission area of the rotary filter 73. The illumination light emanating from the light source 74 does not fall on the light guide 19. Consequently, no illumination light is irradiated to the object 63 from the distal section 61. Eventually, the CCD produces only a video signal representing a pitch-dark image. This cripples succeeding endoscopic diagnosis. Moreover, it is hard to pull the endoscope 52 out of a tortuous body cavity.

In this case, an operator drives the motor 97, which causes the mounting bracket 91, to which the rotary filter 73 and motor 72 are fixed, to slide, so as to rotate it. The operator then removes the rotary filter 73 from the path of light emanating from the light source 74. White light emanating from the light source 74 is irradiated to the object 63 from the distal section 61 of the insertion member 56 by way of the condenser lens 75 and light guide 19. The CCD produces a video signal while being exposed to the white light. With the help of an image displayed according to the video signal, the insertion member 56 of the endoscope 52 is pulled out of the body cavity.

However, the operator has to suspend endoscopic diagnosis because the illumination light is extinguished suddenly in the course of the endoscopic diagnosis or a picture is displayed in a specific color alone. The operator has to restart diagnosis using another electronic endoscope system 51. This poses a problem in that the operator and a person receiving the endoscopic diagnosis alike have to incur a heavy load.

The present invention attempts to break through the foregoing situation. An object of the present invention is to provide an illumination control system and an illumination control method for endoscope systems according to which in case the rotary filter is stopped for some reasons or the rotation of the rotary filter becomes abnormal anyhow, the rotary filter is immediately removed from the path of light emanating from the light source. Nevertheless, supply of illumination light that is white light is continued so that the endoscope can be continuously used. Thus, the load to be imposed on an operator and a person receiving endoscopic examination can be alleviated.

DISCLOSURE OF INVENTION

An illumination control system for endoscope systems in accordance with the present invention comprises:

a rotation detecting section for detecting the rotation of a filter which is located on a path of illumination light emitted from a light source, which irradiates color light rays having different wavelengths to an object, and which is driven by a rotational driver;

an abnormality determination section for determining from the rotation of filter detected by the rotation detecting section whether the rotation state of the filter is normal; and a filter removing section that when the abnormality determination section determines that the rotation state of the filter is abnormal, removes the filter from the path of the illumination light.

According to another aspect of the present invention, an illumination control method for endoscope systems comprises:

a rotation detecting step of detecting the rotation of a filter which is located on a path of illumination light emitted from a light source, which irradiates color light rays having different wavelengths to an object, and which is driven by a rotational driver;

an abnormality determination step of determining from the rotation of filter detected by the rotation detecting step whether the rotation state of the filter is normal; and a filter removing step at which when the abnormality determination step determines that the rotation state of the filter is abnormal, the filter is removed from the path of the illumination light.

According to still another aspect of the present invention, an illumination control system for endoscope systems comprises:

a rotation detecting means for detecting the rotation of a filter which is located on the path of illumination light emitted from a light source, which irradiates color light rays having different wavelengths to an object, and which is driven by a rotational driver;

an abnormality determination means for determining from the rotation of the filter detected by the rotation detecting means whether the rotation state of the filter is normal; and a filter removing means that when the abnormality determination means determines that the rotation state of the filter is abnormal, removes the filter from the path of the illumination light.

BEST MODE FOR CARRYING OUT THE INVENTION

Referring to the drawings, an embodiment of the present invention will be described below.

Figure 1:
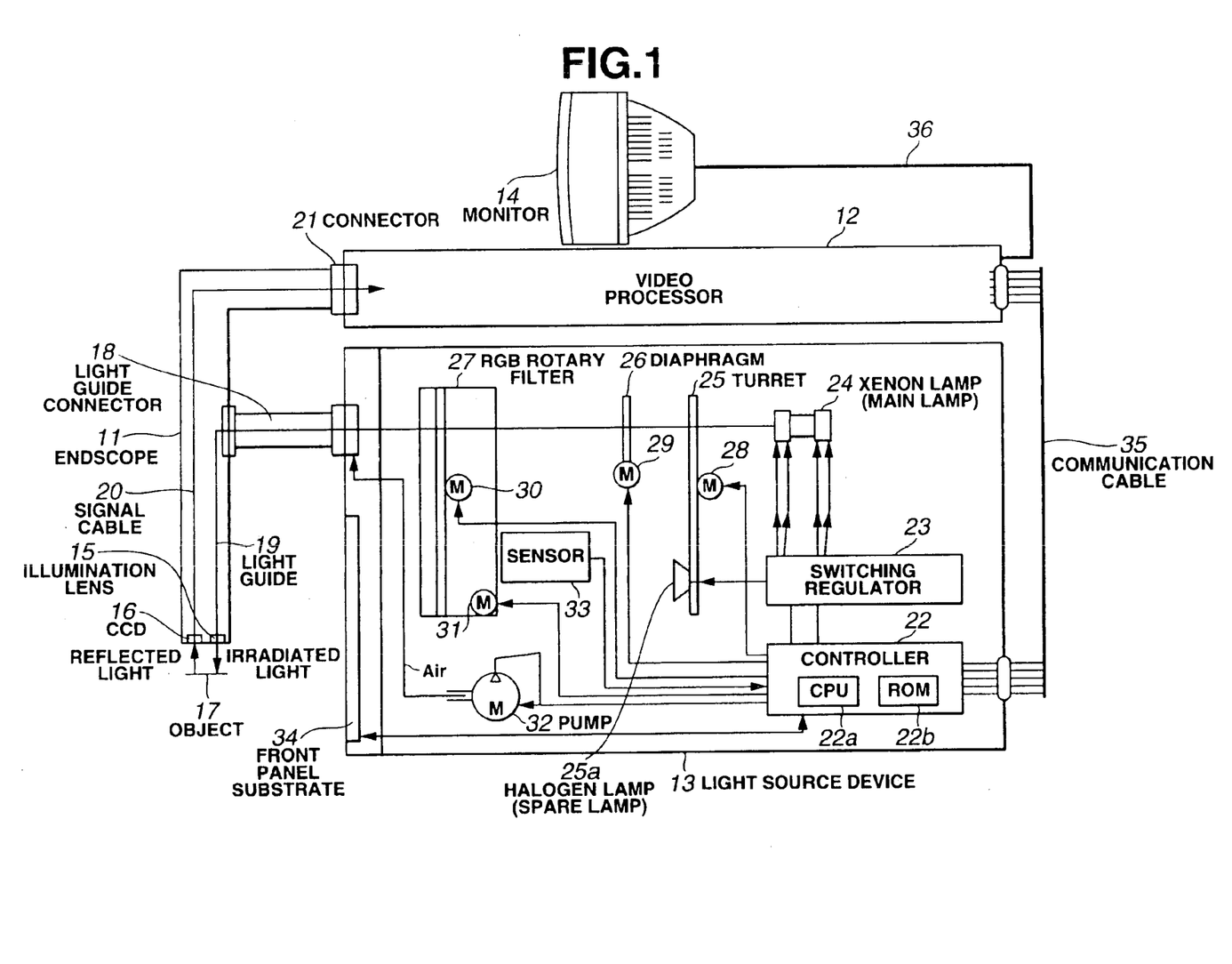
FIG. 1 is a block diagram showing an illumination control systems according to a preferred embodiment of the present invention.

An endoscope system in accordance with the present invention comprises, as shown in FIG. 1, an endoscope (hereinafter, referred to as scope) 11, a video processor 12, a light source device 13, and a monitor 14.

An illumination lens 15 and a CCD 16 are incorporated in the distal section of the endoscope 11. The distal end of a light guide 19 passed through a light guide connector 18 located in the proximal section of the endoscope 11 is coupled to the illumination lens 15. A signal cable 20 passed through a connector 21 located in the proximal section of the endoscope 11 is coupled to the CCD.

The light guide 19 introduces illumination light, which is emitted from a light source 24 included in the light source device, 13 to be described later, to the illumination lens 15, so that the illumination light will be irradiated to an object 17 through the illumination lens 15. The signal cable 20 transmits a driving signal for driving the CCD 16 from the video processor 12, which will be described later, and an object video signal produced by exposing the CCD 16 with object light reflected from the object 17.

The light guide 19 is detachably connected to the light source device 13 through the light guide connector 18. The signal cable 20 is detachably connected to the video processor 12 through the connector 21.

The video processor 12 produces and transfers a driving signal with which the CCD 16 is driven. Moreover, the video processor 12 produces a television video signal from an object video signal produced by exposing the CCD 16 to object light. Furthermore, the video processor 12 produces a video display signal according to which an object image picked up by the CCD 16 is displayed on the monitor 14.

The light source device 13 includes a controller 22, a switching regulator 23, the light source 24, a turret 25, a diaphragm 26, and an RGB rotary filter 27.

The controller 22 is connected to the video processor 12 over a communication cable 35. The switching regulator 23 produces and supplies power, with which the light source 24 is lit, as described later in response to a control signal sent from the controller 22. The light source 24 is lit with power supplied from the switching regulator 23 and emits white light, such as, a xenon lamp. The turret 25 includes a transmission filer that is disposed on the path of the white light emanating from the light source 24 and used to pass the white light, an amount of light reducing filter for reducing the white light so as to provide a predetermined amount of light, a specific wavelength light filter for passing, such as, infrared light alone out of the white light, and an emergency lamp 25a that is lit when the light source 24 cannot be lit, such as, a halogen lamp. The diaphragm 26 controls amount of white light emitted from the turret 25 on the path of the white light emanating from the light source 24. The RGB rotary filter 27 has color filters for three primary colors of red, green, and blue and that passes the white light which is emitted from the light source 24 and of which amount is controlled to a predetermined level by the diaphragm 26. The light source device also includes a pump 32 that supplies water or air to a water/air supply channel lying through the endoscope 11, and a front panel substrate 34 having various buttons for use in giving operational instructions to the light source device 13 and various indicators indicating operating modes.

The controller 22 comprises a CPU 22a that is a microprocessor for controlling the driving of the light source device 13, and a ROM 22b in which various driving control sequences for the light source device 13 and data are held.

The switching regulator 23 includes a stabilizing circuit that produces power with which the light source 24 is lit and that stabilizes the power. Under the control of the controller 22, the switching regulator 23 supplies power to the light source 24 or stops supplying power and controls a current used to light the light source.

The turret 25 is shaped substantially like a disk having the aforesaid transmission filter, amount of light reducing filter, specific wavelength-light filter, and emergency lamp 25a arranged on the perimeter thereof. The center shaft of the disk is fixed to the shaft of a motor 28. The motor 28 is driven to rotate under the control of the controller 22, so that a predetermined filter or the emergency lamp 25a will be located on the ray axis of the white light emanating from the light source 24.

When a motor 29 is driven under the control of the controller 22, the diaphragm 26 limits the amount of white light, which is emitted from the light source 24 and passed through the turret 25, to a predetermined level.

The RGB rotary filter 27 is identical to the above described rotary filter 73 (see FIG. 6 and FIG. 7) and shaped like a disk having the color transmission filters 73R, 73G, and 73B of red (R), green (G), and blue (B) arranged equidistantly. The portion of the disk interposed between each pair of the color transmission filters 73R, 73G, and 73B does not pass the white light emanating from the light source 24. Moreover, the white light is transmitted as color light rays of red, green, and blue by the color transmission filters 73R, 73G, and 73B. When a motor 30 (corresponding to the motor 72 in FIG. 6 and FIG. 7) is driven to rotate at a predetermined rotating speed and a predetermined rps under the control of the controller 22, illumination light rays of red (R), green (G), and blue (B) passed through the RGB rotary filter 27 are irradiated to the object 17 by way of the light guide 19 and illumination lens 15. The CCD 16 is exposed to reflected object light of each of the red, green, and blue illumination light rays, whereby red, green, and blue object video signals are produced. Consequently, field-sequential imaging video signals are produced.

Moreover, the RGB rotary filter 27 is removed from the path of the white light emanating from the light source 24 by means of a motor 31 under the control of the controller 22. The motor 31 corresponds to the motor 97 in FIG. 7. The mechanism for removing the RGB rotary filter 27 from the light path is identical to the one shown in FIG. 7.

Figure 6:
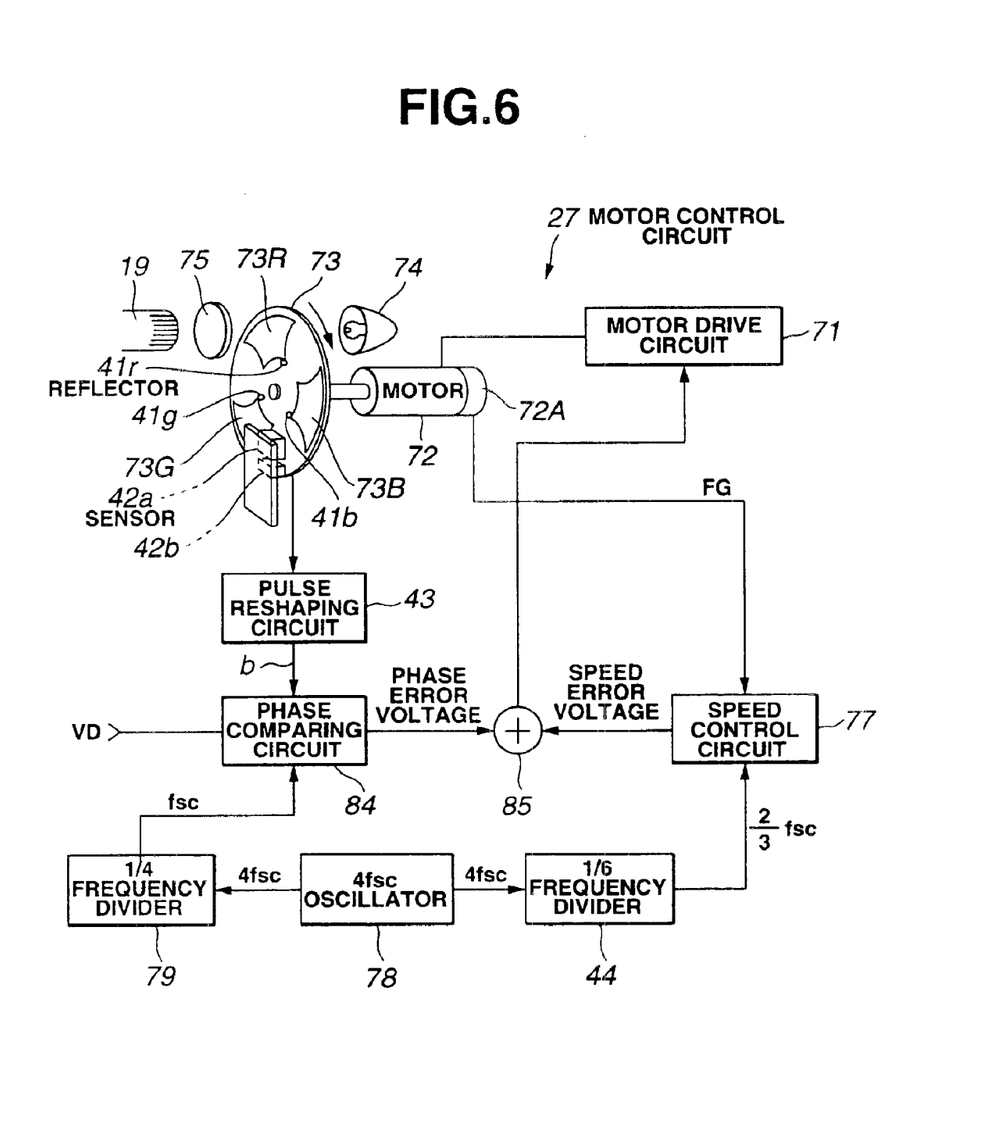
FIG. 6 is a block diagram showing a rotary filter included in the conventional endoscope system and presenting a mechanism for controlling the driving of the rotary filter.

Furthermore, the rotary filter 73 shown in FIG. 6 has the reflectors 41r, 41g, and 41b that give indices of color transmission open periods for red, green, and blue light rays. Similarly to the rotary filter 73, the RGB rotary filter 27 has a reflector. However, the RGB rotary filter 27 has the reflector only at a reference point that is the start point of the first open period. A sensor 33 is included for detecting the reflector indicating the reference point. The result of the detection performed by the sensor 33 is transferred to the controller 22.

Various operating buttons and operational indicators, for example, LEDs are mounted on the front panel substrate 34. For the operational indication, a display means is included so that when an abnormality or a failure occurs in the light source device 13, the abnormality or failure can be notified. An abnormality notifying means is, for example, a mechanism for causing a red LED to flicker or a means for notifying a user of an abnormality by sounding a sounding device.

When an operating button on the front panel substrate is manipulated, the information that the operating button has been manipulated is transmitted to the controller 22. In the controller 22, the CPU 22a reads a sequence and data associated with the operating button from the ROM 22b. Based on the read sequence and data, the CPU 22a controls the driving of the switching regulator 23, motors 28 to 31, and pump 32.

Figure 2A:
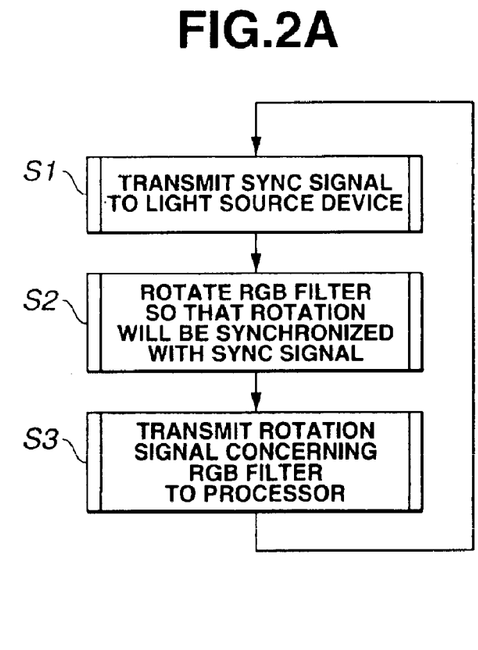
FIG. 2A and FIG. 2B are flowcharts describing routines performed according to the illumination control system and illumination control method for endoscope systems in accordance with the embodiment.
Figure 2B:
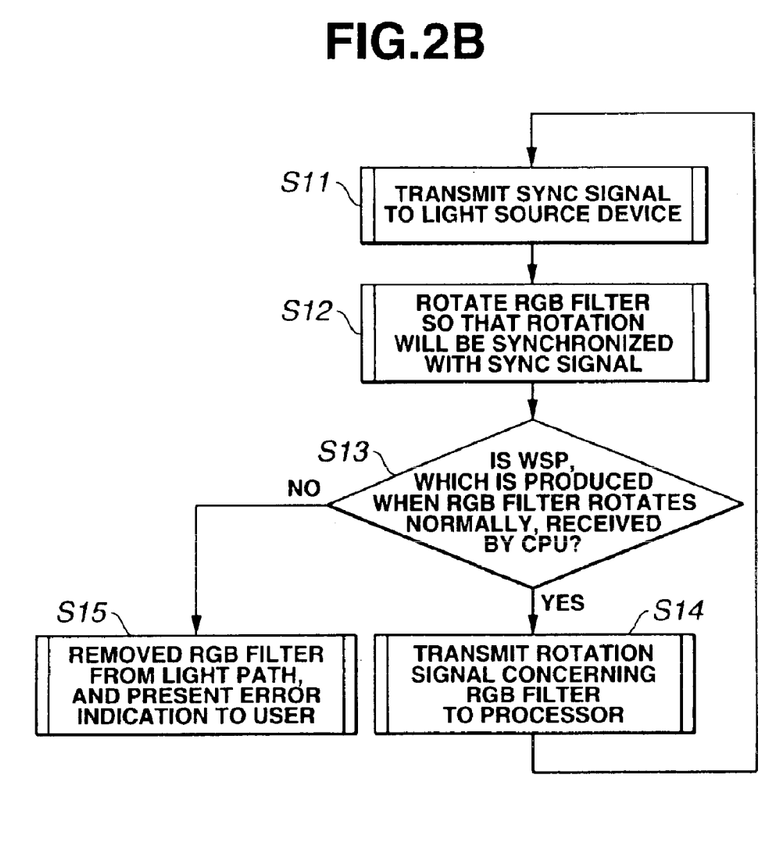
Figure 3A:
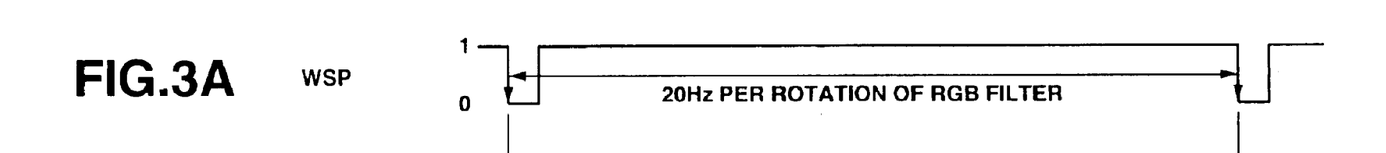
FIG. 3A and FIG. 3B are timing charts for explaining normal routines performed according to the illumination control system and illumination control method for endoscope systems in accordance with the embodiment.
Figure 3B:
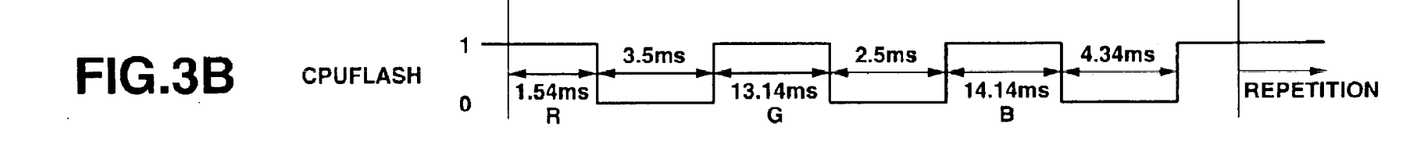
Figure 4A:
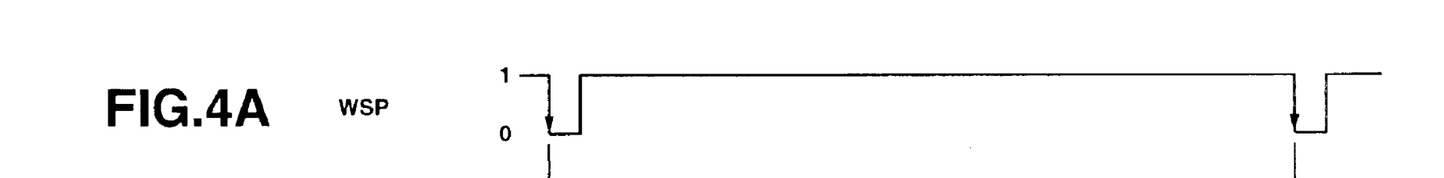
FIG. 4A and FIG. 4B are timing charts for explaining specific routines performed according to the illumination control system and illumination control method for endoscope systems in accordance with the embodiment.
Figure 4B:
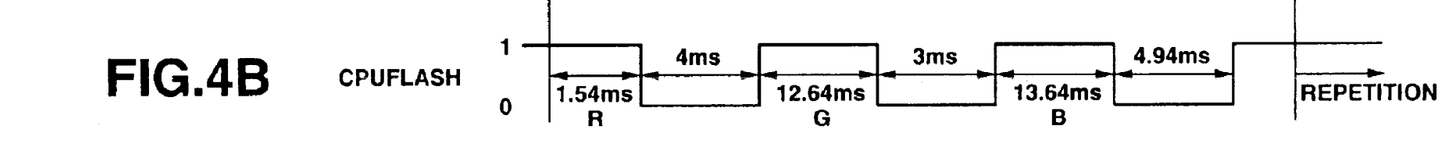

Referring to FIG. 2 to FIG. 4, the rotational driving of the RGB rotary filter 27 and the control of power to be supplied from the switching regulator 23 to the light source 24, which are performed in the endoscope system having the foregoing components, will be described below.

To begin with, referring to FIG. 3A and FIG. 3B, a description will be made of routines performed in the endoscope system during normal diagnosis. Under the control of the controller 22, the motor 30 for the RGB rotary filter 27 is driven to rotate. The rotational driving of the motor 30 is, as shown in FIG. 3A, controlled so that pulses will be produced at 20 Hz during one rotation of the RGB rotary filter 27. The sensor 33 detects the reflector that indicates the reference point on the RGB rotary filter 27 which is driven so that pulses will be produced at 20 Hz during one rotation of the RGB rotary filter. At the trailing edge of a WSP (Write Start Pulse) produced by the sensor 33, as shown in FIG. 3B the controller 22 controls the driving of the CCD 16 using the video processor 12 so that the red (R) transmission filter of the RGB rotary filter 27 will lie on the path of light emanating from the light source 24 for 1.54 ms. Thereafter, red light propagated from the red transmission filter will be irradiated to the object 17, and the CCD 16 will pick up a red object picture. In other words, the period of 1.54 ms since the trailing edge of the WPS serves as a red image production period during which the CCD 16 is exposed to reflected red light and produces a red image.

After the elapse of the red (R) image production period, the non-transmission area of the RGB rotary filter 27 that is interposed between the red transmission filter and green transmission filter and that intercepts illumination light lies on the light path for 3.5 ms. During the period of 3.5 ms, the controller 22 captures a red video signal, which is produced by the CCD 16 exposed to reflected red illumination light, into the video processor 12. That is to say, this period serves as a red video signal capturing period.

After the elapse of the red video signal capturing period, as shown in FIG. 3B, a green (G) image production period, a green video signal capturing period, a blue (B) image production period, and a blue video signal capturing period succeed. Namely, while the RGB rotary filter makes one rotation, the red, green, and blue video signals are captured into the video processor 12.

FIG. 4A and FIG. 4B demonstrate that the red (R), green (G), and blue (B) image production periods and the red, green, and blue video signal capturing periods are different from one another and adopted for specific diagnosis using the endoscope system in which the present invention is implemented.

Referring to FIG. 2, a description will be made of a control sequence by the controller 22 that controls the rotational driving of the RGB rotary filter 27 and the driving of the video processor 12. Herein, the video processor 12 exposes the CCD 16 to light for imaging and captures a video signal produced by the exposed CCD 16. For normal endoscopic diagnosis, the turret 25 selects the transmission filter which does not reduce illumination light emitted from the light source 24. The diaphragm 26 is set so that a predetermined amount of light will be emitted to the RGB rotary filter 27.

FIG. 2A describes routines performed when the endoscope system is driven normally, for example, when the endoscope system is driven for normal diagnosis as shown in FIG. 3A and FIG. 3B or when the endoscope system is driven for specific diagnosis as shown in FIG. 4A and FIG. 4B. At step Si, the controller 22 included in the light source device 13 captures a synchronizing (sync) signal contained in a video signal produced by the video processor 12 over the communication cable 35. Based on the sync signal captured at step S1, the controller 22 controls the rotational driving of the RGB rotary filter 27 synchronously with the sync signal. At step S3, a rotation signal indicating that the RGB rotary filter 27 is rotating is transmitted to the video processor 12, and process is returned to step S1. Namely, the rotational driving of the RGB rotary filter 27 is monitored all the time so that the rotation of the RGB rotary filter 27 will be synchronized with the sync signal indicating the timing according to which the video processor 12 captures an object video signal from the CCD 16. Whether the rotation of the RGB rotary filter 27 is synchronized with the sync signal is determined by comparing the leading edge of a WSP, which the reflector located at the reference point and detected by the sensor 33 produces, with the sync signal which the video processor 12 produces for each field by mixing red, green, and blue video signals. When the rotation is not synchronized with the capturing, the rotational driving of the motor 30 for the RGB rotary filter 27 which is not shown is corrected so that the rotation and the capturing will be synchronized with each other.

Next, referring to FIG. 2B, a description will be made of routines performed in case the rotational driving of the motor 30 for the RGB rotary filter 27 is stopped for some reasons.

At step S11, the controller 22 captures a sync signal from the video processor 12. At step S12, the rotational driving of the RGB rotary filter 27 is controlled so that the rotation of the RGB rotary filter will be synchronized with the sync signal captured from the video processor 12 at step S11.

At step S13, the controller 22 drives the RGB rotary filter 27 so that the RGB rotary filter 27 will rotate normally, and determines whether a WSP is sent from the sensor 33 at predetermined intervals.

When it is determined at step S13 that the WSP is sent from the sensor 33 at predetermined intervals, at step S14 a rotation signal indicating that the RGB rotary filter 27 is rotating is transmitted to the video processor 12. Program is then returned to step S11. In other words, when the RGB rotary filter 27 is rotating normally, the same control sequence as the one described in FIG. 2A is followed.

When the rotational driving of the motor 30 for the RGB rotary filter 27 is stopped for some reasons, the WSP is not sent from the sensor 33 at predetermined intervals. It is then determined at step S13 that the WSP indicating that the RGB rotary filter 27 is driven to rotate is not sent from the sensor 33 at predetermined intervals. At step S15, the controller 22 drives the motor 31 that removes the RGB rotary filter 27 from the path of illumination light emitted from the light source 24, so that the RGB rotary filter 27 will be removed from the light path. Moreover, the red indicator LED for an emergency mounted on the front panel substrate 34 is caused to flicker or a sounding means is driven in order to generate a sound for notifying of an emergency.

Specifically, when the rotational driving of the motor 30 is stopped, the RGB rotary filter 27 is stopped, for example, with any of the red, green, and blue transmission filters located on the path of white light emanating from the light source 24 or with the non-transmission area between any pair of the red, green, and blue transmission filters located thereon. Consequently, illumination light irradiated from the illumination lens 15 to the object 17 is one of the red, green, and blue light rays. Otherwise, no illumination light is irradiated. Therefore, an object picture picked up under one of the red, green, and blue light rays is dark. It is difficult for the operator to interpret a display image displayed on the monitor 14. When the non-transmission area is located on the light path, no illumination light is irradiated to the object 17. A picture picked up by the CCD 16 is therefore pitch-dark. A display image displayed on the monitor 14 is a pitch-dark image.

Owing to the abnormality notification of step S15, an operator is aware of the abnormality occurring in the endoscope system. At step S15, the removal motor 31 for the RGB rotary filter 27 is driven in order to remove the RGB rotary filter 27 from the light path. Illumination light emitted from the light source 24 is propagated by way of the turret 25, diaphragm 26, light guide connector 18, light guide 19, and illumination lens 45. Consequently, white light is irradiated to the object 17.

The CCD 16 can produce a video signal representing the object illuminated with white light. The video signal produced by the exposed CCD 16 is captured into the video processor 12. Consequently, a monochrome video signal is produced. According to a display signal produced from the monochrome video signal, a monochrome display image is displayed on the monitor 14. An operator is notified of an abnormality. Based on the monochrome display image displayed on the monitor 14, the operator can pull out the endoscope 11 from a body cavity. When the monochrome display image enables diagnosis or cure, the operator can continue endoscopic diagnosis.

At this time, illumination light emitted from the light source 24 and irradiated to the object 17 may be too bright, and a picture represented by a video signal produced by the exposed CCD 16 may be too bright. In this case, the motor 29 for the diaphragm 26 is driven in order to adjust amount of light. Otherwise, the motor 28 for the turret 25 is driven so that the light reducing filter mounted on the turret 25 will be located on the path of light emitted from the light source 24 in order to reduce amount of light. Otherwise the switching regulator 24 is controlled in order to reduce power to be supplied to the light source 24. Thus, amount of light that is irradiated to the object 17 and reflected therefrom and that falls on the CCD 16 is set to a predetermined amount of light. This results in a monochrome display image that is easy for an operator to interpret.

The embodiment of the present invention has been described so far. The present invention is not limited to the embodiment. Needless to say, various modifications can be made without a departure from the spirit of the present invention.

What is claimed is:

1. An illumination control system comprising:
   a rotation detecting section for detecting the rotation of a filter which is located on a path of illumination light emitted from a light source, which irradiates color light rays having different wavelengths to an object, and which is driven by a rotational driver;
   an abnormality determination section for determining whether status of filter rotation is normal or abnormal based on the detected rotation of the filter by the rotation detecting section; and
   a filter removing section that removes the filter from the path of the illumination light when the abnormality determination section determines that the status of filter rotation is abnormal.

2. An illumination control system according to claim 1, further comprising:
   a supplied light amount control section that reduces an amount of the illumination light emitted from the light source when the abnormality determination section determines that the status of the filter rotation is abnormal and when the filter removing section removes the filter from the path of the illumination light.

3. An illumination control system according to claim 1, wherein when the abnormality determination section determines that status of the filter rotation is abnormal, a video processor produces a monochrome video signal.

4. An illumination control system according to claim 1, wherein: the rotation detecting section includes a position indicator that is located at a reference point on the filter, and a sensor that detects the position indicator; the sensor detects the position indicator for every rotation of the filter.

5. An illumination control system according to claim 2, the supplied light amount control section for reducing amount of the illumination light includes a diaphragm adjusting device for adjusting a diaphragm located on the path of the illumination light so as to reduce amount of the illumination light to be irradiated to an object.

6. An illumination control system according to claim 2, wherein the supplied light amount control section for reducing amount of the illumination light includes a current regulator for regulating a current with which the light source is lit so as to reduce the illumination light to be irradiated to an object.

7. An illumination control system according to claim 2, wherein the supplied light amount control section for reducing amount of the illumination light includes an amount of light adjusting filter located on the path of the illumination light so as to reduce the illumination light to be irradiated to an object.

8. An illumination control system according to claim 1, further comprising a notifying section that when the abnormality determination section determines that the status of the filter rotation is abnormal, notifies a user of an abnormality of the rotation of the filter.

9. An illumination control method for endoscope systems comprising:
   detecting rotation of a filter, located on a path of illumination light emitted from a light source, which irradiates color light rays having different wavelengths to an object, and which is driven by a rotational driver;
   determining whether status of filter rotation is normal or abnormal based on the detected rotation of the filter; and
   removing the filter from the illumination path of the illumination light when the status of the filter rotation is determined to be abnormal.

10. An illumination control method according to claim 9, further comprising:
    reducing an amount of the illumination light emitted from the light source when the status of the filter rotation is determined to be abnormal and when the filter is removed from the path of the illumination light.

11. An illumination-control method according to claim 10, wherein the amount of the illumination light is reduced by adjusting a diaphragm located on the path of the illumination light.

12. An illumination control method according to claim 10, wherein the amount of the illumination light is reduced by regulating a current supplied to the light source.

13. An illumination control method according to claim 10, wherein the amount of the illumination light is reduced by placing a light amount controlling filter on the path of the illumination light.

14. An illumination control method according to claim 9, further comprising:
    notifying a user that the status of the filter rotation is abnormal when the status of the filter rotation is determined to be abnormal.

15. An illumination control system comprising:
    a rotation detecting means for detecting the rotation of a filter which is located on a path of illumination light emitted from a light source, which irradiates color light rays having different wavelengths to an object, and which is driven by a rotational driver;
    an abnormality determination means for determining whether status of filter rotation is normal or abnormal based on the detected rotation of the filter by the rotation detecting means; and
    a filter removing means that removes the filter from the path of the illumination light when the abnormality determination means determines that the status of filter rotation is determined to be abnormal.

16. An illumination control system according to claim 15, further comprising a supplied light amount control means reduces an amount of the illumination light emitted from the light source and supplied to an endoscope when the abnormality determination means determines that status of filter rotation is abnormal and when filter removing means removes the filter from the path of the illumination light.

* * * * *